United States Patent [19]

McCurry et al.

[11] Patent Number: 5,003,057

[45] Date of Patent: Mar. 26, 1991

[54] PROCESS FOR PRODUCTION OF GLYCOSIDES

[75] Inventors: Patrick M. McCurry; William Kozak; Carl Pickens, all of Decatur, Ill.

[73] Assignee: Henkel Kommanditgesellschaft auf Aktien, Duesseldorf, Fed. Rep. of Germany

[21] Appl. No.: 289,950

[22] Filed: Dec. 23, 1988

[51] Int. Cl.$^5$ .......................... C07G 3/00; C08B 37/00
[52] U.S. Cl. ..................................... 536/186; 536/4.1
[58] Field of Search ................................ 536/18.6, 4.1

[56] References Cited

U.S. PATENT DOCUMENTS

| | | | |
|---|---|---|---|
| 3,219,656 | 11/1965 | Boettner | 260/210 |
| 3,547,828 | 12/1970 | Mansfield et al. | 252/351 |
| 3,598,865 | 9/1971 | Lew | 260/210 |
| 3,839,319 | 10/1974 | Greminger et al. | 536/91 |

FOREIGN PATENT DOCUMENTS 132043 8/1984 European Pat. Off. .

*Primary Examiner*—Ronald W. Griffin
*Assistant Examiner*—Everett White
*Attorney, Agent, or Firm*—Ernest G. Szoke; Wayne C. Jaeschke; Daniel S. Ortiz

[57] ABSTRACT

A process for preparing glycosides from a source of saccharide moiety and an alcohol in the presence of a hydrophobic acid catalyst is provided. An example of such a catalyst is dinonylnaphthalenemonosulfonic acid. The use of such catalysts provides a number of process advantages, which includes the reduced production of polar by-products. Preferred glycosides produced by the process are higher alkyl glycosides useful as surfactants.

8 Claims, No Drawings

PROCESS FOR PRODUCTION OF GLYCOSIDES

BACKGROUND OF THE INVENTION

1. Field of the Invention:

This invention relates to the production of glycosides by the reaction of an alcohol with a reducing saccharide, or a source of reducing saccharide, in the presence of an acid catalyst.

2. Statement of Related Art:

The reaction of a reducing saccharide, e.g. an aldose or ketose saccharide, or a source thereof, with an alcohol results in the formation of a glycoside. Acids catalyze the reaction between a reducing saccharide and an alcohol. When the alcohol is an alkanol, the resulting glycoside is commonly referred to as an alkyl glycoside. Alkyl glycosides are generally stable to alkali. Long chain alkyl groups contribute to surface activity, e.g. detergency, of the glycoside.

U.S. Pat. No. 3,547,828 (Mansfield et al.) discloses a process for producing surface active (i.e. higher alkyl) glycosides by first reacting a saccharide with a lower alkanol (e.g. butanol) in the presence of an acid catalyst to form a lower alkyl glycoside which is then reacted with a higher alkanol to form the higher alkyl glycoside. The acid catalysts disclosed by Mansfield et al. are mineral acids ($H_2SO_4$, HCl and $HNO_3$), p-toluenesulfonic acid, and methanesulfonic acid. It is stated by Mansfield et al. that while other acid, electron accepting compounds of the group generally classified as "Lewis acids" may be employed as catalysts, sulfuric acid is preferred.

U.S. Pat. No. 3,598,865 (Lew) discloses the production of higher alkyl ($C_8$-$C_{25}$) glycosides from a monosaccharide or source thereof and a higher monohydric alcohol in the presence of a latent solvent (lower alcohols) and an acid catalyst selected from the group consisting of sulfuric acid, hydrochloric acid, phosphoric acid, phosphorous acid, toluenesulfonic acid, and boron trifluoride.

U.S. Pat. No. 3,219,656 (Boettner) discloses a process for producing a higher alkyl glycoside by reacting glucose with methanol in the presence of a macroreticular-structured sulfonic acid resin, anhydrous and in the acid form, to produce methyl glucoside which is reacted without isolation with butanol to form butyl glucoside and which in turn is reacted with a higher alcohol to form a surface active higher alkyl glycoside.

U.S. Pat. No. 3,839,319 (Mansfield) discloses a process for producing alkyl glycosides by direct, acid catalyzed reaction of a higher alcohol and a saccharide. The acid catalysts are mineral acids such as hydrochloric and sulfuric, and sulfonic acid exchange resins.

E.P.O. Publication No. 132,043, published Jan. 23, 1985, (Davis et al.) discloses the production of alkyl glycosides by reacting, in the presence of an acid catalyst, a monohydric alcohol with a monosaccharide or a source thereof, wherein the acid catalyst is the acid form of an anionic surfactant, e.g. alkyl hydrogen sulfates or alkyl sulfonic acids having in their molecular structure an alkyl group containing from 8 to 22 carbon atoms and alkylbenzene sulfonic acid, with alkyl groups having from 8 to 15 carbon atoms. The publication states it is contemplated by Davis et al. that the catalyst gives a faster reaction rate by building up on the surface of solid saccharide particles which is facilitated by the surface active properties of the catalyst.

While the above processes have varying degrees of utility, they each suffer from one or more disadvantages such as inefficient multi-phase reactions, insufficient reaction rates, excessive by-product formation (e.g. polydextrose), excessive color formation, as well as others. Accordingly, it is desirable to provide a new process which does not suffer from one or more of the disadvantages in the above processes.

SUMMARY OF THE INVENTION

This invention relates to a process of preparing glycosides from a saccharide and an alcohol which employs as the acid catalyst a strong, organic acid that is hydrophobic. Conventional catalysts for the reaction are hydrophilic by comparison and do not give the performance advantages obtained with the catalysts used in this invention. Advantages that result from the use of a hydrophobic catalyst include increased productivity (in terms of product solids) from the reactor, decreased foaming in the reactor, and elimination of carbonization of the product mixture during distillation or evaporation of excess alcohol reactant.

This invention also relates to a process of preparing glycosides comprising reacting, in the presence of an acid catalyst, an alcohol with a source of saccharide moiety, said acid catalyst (a) being comprised of an organic-sulfonic acid having at least 8 carbon atoms and (b) having less than about 2% of a source of sulfuric acid, said 2% being on the basis of weight as sulfuric acid by weight of said acid catalyst. While Davis et al. discloses the use of particular organic-sulfonic acids that are nominally organic-sulfonic acids (e.g. dodecylbenzenesulfonic acid), it has been found that the commercially available materials of this type often contain a small, but significant, amount of sulfuric acid or a source thereof, (i.e. up to 2% sulfuric acid by weight). This small amount has been found to have a significant effect on the selectivity of the catalyst for the glycosidation reaction between the alcohol and the source of saccharide moiety.

Similarly, this invention also relates to a process of preparing glycosides comprising:

(a) reacting, to form an acid catalyst, a composition comprised of an organic-sulfonic acid and a source of sulfuric acid, with a material reactive with said source, the amount of said reactive material being (i) sufficient to convert at least a portion of said source of sulfuric acid to a member selected from the group consisting of hydrophobic acids, non-acidic salts, and mixtures thereof, and (ii) insufficient to convert the majority of the organic-sulfonic acid in said composition to an organic-sulfonate, and (b) reacting, in the presence of said acid catalyst, an alcohol having more than four carbon atoms with a source of saccharide moiety.

DETAILED DESCRIPTION OF THE INVENTION

The process of this invention employs an acid catalyst that is hydrophobic in nature, i.e. more hydrophobic than catalysts conventionally used to produce glycosides, from saccharides and alcohols.

A useful measure of the hydrophobicity of the acid catalyst is the hydrophilic/lipophilic balance, commonly referred to as the HLB, of the catalyst. In general, the acid catalyst should have an HLB of less than about 13, and more preferably less than about 10. Particularly preferred acid catalysts will have an HLB less than about 8 and more preferably less than about 6, e.g. less than about 3.

Another useful measure of the hydrophobicity of the acid catalysts is the partition coefficient of the acid catalyst between an oil, e.g. dodecanol, and water. This measure is particularly useful for acid catalysts for which published HLB values are unreliable or unavailable and/or reliable experimentally determined HLB values are difficult or impractical to obtain. The acid catalyst should partition in the oil layer to a greater extent than the conventional acid catalysts, i.e. should have an oil/water partition coefficient greater than the conventional acid catalysts. Preferred acid catalysts should partition predominantly in oil (i.e. a partition coefficient greater than 1.0), more preferably strongly in oil e.g. 2:1, 5:1, or 10:1, and most preferably overwhelmingly in oil, e.g. 50:1 100:1, 1000:1 or greater. In other words, the most preferred hydrophobic catalysts are insoluble (i.e. practically insoluble) in water.

Another useful measure of the hydrophobicity is the selectivity of the catalyst in producing non-polar reaction products rather than polar by-products (e.g. polydextrose and very high degree of polymerization (D.P.) alkyl glycosides). Hydrophobic catalysts will produce less polar by-products, all other conditions being equal, than conventional catalysts. The amount of polar by-products can be easily measured, particularly with relatively low D.P. alkyl glycoside products, by contacting the reaction produot mixture with water to extract the polar by-products and measuring the solids extracted (with a correction for any residual dextrose starting material).

The preferred acid catalysts fall into two broad and different chemical classifications: one characterized as strong organic acid compounds and the other characterized as condensation or addition polymers (including oligomers) comprised of units attributable to a strong acid monomer (e.g. styrenesulfonic acid) and a hydrophobic mono-olefinic monomer. By "strong acid" is meant an acid having significant catalytic activity with respect to glycoside formation from a saccharide and an alcohol, e.g. an acid having a pKa of less than about 1, more preferably less than about 0. Typical strong, hydrophobic acids are organic-sulfonic acids (e.g. alkylsulfonic acids and alkylarenesulfonic acids) which have a sufficient number of carbon atoms in the organic group to render the acid hydrophobic. As used herein, "organic-sulfonic acids" refers to sulfonic acids having a carbon based moiety covalently bonded to the sulfur atom of the sulfonic acid moiety. Sulfonic acids in general are discussed in Kirk-Othmer, *Encyclopedia of Chemical Technology*, Vol. 22, pp. 45-61 (John Wiley & Sons, 1983) the pertinent disclosures of which are incorporated herein by reference. The preparation and properties of organic-sulfonic acids are extensively discussed in C. M. Suter, *The Organic Chemistry of Sulfur* (John Wiley & Sons, 1944), the pertinent disclosures of which are incorporated by reference.

Examples of the strong organic acids useful as catalysts include alkylsulfonic acids, alkylarenesulfonic acids, dialkyl esters of sulfosuccinic acids, and alkylarols (i.e. alkyl substituted hydroxy-aromatic compounds), said alkylarols having sufficient electrophilic aromatic substituents to raise the acidity thereof to a catalytic level, e.g. nitrated alkyl phenols. Preferred strong organic acids are alkylmonosulfonic acids, alkylarenemonosulfonic acids, aralkylarenemonosulfonic acids, or dialkyl esters of sulfosuccinc acids said acids having a sufficient number of carbon atoms to lower the HLB to less than about 13, more preferably less than about 8. Preferred strong organic acids include dialkylnaphthalenemonosulfonic acids (e.g. dinonylnaphthalenemonosulfonic acid) and aralkylnaphthalenemonosulfonic acids (e.g.(1-phenylethyl)naphthalenemonosulfonic acid and (naphthylmethyl)naphthalenemonosulfonic acid). Compositions comprised of dinonylnaphthalenesulfonic acid are described in U.S. Pat. No. 3,957,859 (Thielcke) and are commercially available from King Industries, Inc. as Nacure 1052, a 50% solution in heptane. Compositions comprised of (1-phenylethyl)naphthalenesulfonic acid can be made by the reaction of styrene with naphthalene (e.g. as described in *Styrene: Its Copolymers and Derivatives*, p. 873 (ACS Monograph Series, Boundy et al. ed., Reinhold Publ. Corp., (1952)) and mono-sulfonating of the resulting product (e.g. with sulfuric acid and/or sulfur trioxide). Compositions comprised of (naphthylmethyl)naphthalenesulfonic acid can be made by condensing naphthalene and formaldehyde in a molar ratio of 2:1, respectively, and sulfonating with an effective molar equivalent of sulfonating agent ($\frac{1}{2}$ molar on the basis of the condensed naphthalene). Mixtures of catalysts are useful in the practice of the invention.

Examples of the polymers include oligomers and relatively low molecular weight polymers comprised of units derived from mono-olefinic strong acids (e.g. styrenesulfonic acid and acrylamidomethylpropane-sulfonic acid) and units derived from mono-olefinic hydrophobic monomers (e.g. styrene, vinyl toluene, vinyl naphthalene, α-methyl styrene and, 2-ethylhexyl acrylate). Particular examples of such a polymer are (i) linear oligomers or low molecular weight addition polymers comprised of repeating units of styrenesulfonic acid and repeating units of styrene and (ii) partially sulfonated condensation polymers of naphthalene and formaldehyde (i.e. partially sulfonated poly(methylenenaphthalene)). The former polymers are conveniently prepared by partially desulfonating (e.g. by treatment with steam) a water-soluble polystyrenesulfonic acid resin to increase the hydrophobicity thereof. The latter are typically prepared by condensing naphthalene with formaldehyde in the presence of sulfuric acid or a source thereof under conditions which (i) sulfonate only a portion (e.g. about one-half) of the naphthyl groups in the polymer or (ii) fully mono-sulfonate each naphthyl group followed by partial desulfonation. Such resins should have a sulfonic acid functionality that will allow the acid form of the resin to partition between oil and water predominantly, if not practically completely, in the oil phase.

The acid catalyst used in the reaction should contain minimal amounts, if any, of hydrophilic acids. For example, a sample of hydrophobic catalyst nominally available from commercial sources as "dinonylnaphthalenesulfonic acid" may contain substantial amounts of alkylnaphthalenedisulfonic acids and/or sulfuric acid. These acids should be removed or rendered non-acidic and/or non-polar prior to use as a catalyst. Removal encompasses extraction with water or dilute base. Residual sulfuric acid can be reacted by heating with (i) fatty alcohol to form relatively non-polar half-acid sulfate esters of the fatty alcohol and thus render the sulfur acid relatively non-polar or (ii) reactive hydrophobic organic compounds, for example alkoxyarenes, e.g. dodecyloxybenzene, to form relatively non-polar organic-sulfonic acids. Partial neutralization of the catalyst can be accomplished by adding an amount of an alkaline material sufficient to neutralize the hydrophilic acids, but insufficient to deleteriously affect the catalytic activity of the remaining hydrophobic acids. The amount of alkaline material needed to accomplish the desired neutralization can be determined from the acid equivalents of the catalyst composition due to the hydrophilic acids and from the total acid equivalents of the acid catalyst. (Of course, the acids will most probably exist in equilibrium within the sample, but the equilibrium should favor neutralization of the more hydrophilic acids in preference to the hydrophobic acids.) These methods can be used singly or in combination as appropriate. Their use should typically so lower the hydrophilic acid content of the nominal hydrophobic catalyst that such catalyst can be regarded as essentially free, if not practically entirely free, of hydrophilic acids.

The amount of acid catalyst used in the process of this invention will generally be a catalytic amount,, i.e. an amount that is less than stoichiometric, but is still sufficient to significantly increase the rate of reaction between the saccharide and alcohol. Preferred amounts will range from about 0.001 to about 0.05 moles per mole of reducing monosaccharide, more preferably from about 0.005 to about 0.025 moles on the same basis.

Without wishing to be bound by any theory unless expressly indicated otherwise, it is believed that the hydrophobic catalyst minimizes bimodal reactions which form small, but important, amounts of very high D.P. (e.g. D.P. greater than 3) glycosidic species (for example, at the interface of separate aqueous and alcohol phases whether or not visible as such) which catalyze the formation of polydextrose and/or more high D.P. glycosidic species. This theory is based, in part, on the observation that prior catalysts appeared to promote the formation of very high D.P. species as well as polydextrose and that the rate of formation of these materials was much greater during the latter period of the reaction leading to a sort of "autocatalytic" reaction producing by-products during such latter period. It is thought that because the hydrophobic catalysts minimize the formation of these high D.P. species, an "autocatalytic" reaction to form by-products is avoided.

The process of reacting the saccharide and alcohol can be otherwise generally conventional, i.e. the process employs reactants and reaction conditions that are otherwise within the ordinary skill of the glycoside production art. The reaction conditions employed can be those disclosed in the general description section of E.P.O. publication No. 132,043, published Jan. 23, 1985 (Davis et al.), the pertinent portions of which are incorporated herein by reference.

Saccharides useful in the process of this invention are saccharides that can be alkylated in the "1" position, commonly referred to as "reducing saccharides", or higher saccharides that can be hydrolyzed to provide such a saccharide. These saccharides are typically comprised of aldo- or keto-hexoses or pentoses.

Examples of saccharides include glucose (dextrose), fructose, mannose, galactose, talose, allose, altrose, idose, arabinose, xylose, lyxose, ribose. Examples of hydrolyzable saccharides that are a source of reducing saccharides include starch, maltose, sucrose, lactose, maltotriose, xylobiose, mellibiose, cellobiose, raffinose, stachiose, methyl glycosides, butyl glycosides, levoglucosan, and 1,6-anhydroglucofuranose.

The physical form of the saccharide may vary. The saccharide will typically be in a fluid (as opposed to a solid) state, e.g. as a melt or an aqueous syrup, during at least a portion of the period of reaction, if not for a predominant portion of the period of the reaction. Crystalline (e.g. anhydrous or hydrates) or amorphous saccharide solids in various particle sizes, e.g. granules, powders, etc., can be used, but the heating of the reaction medium may well fluidize at least a portion of a solid reactant, if not a predominant portion of the saccharide reactant. Aqueous syrups of saccharides, typically at saccharide solids of between about 10% and 90% dry solids by weight can also be used. Indeed, the use of the hydrophobic catalysts of this invention should show the most improved results over conventional catalysts in the context of the use of aqueous syrup reactants as compared with processes which employ solid saccharide reactants, particularly with respect to avoiding the formation of deleterious amounts of polysaccharides and very high DP alkyl glycosides during the glycoside formation reaction.

The preferred saccharides are glucose, galactose, xylose and arabinose, or mixtures thereof, for reasons of availability, low cost, and convenience. Glucose in the anhydrous crystalline form is preferred, although dextrose monohydrate, corn syrups of high dry solids (typically 50% to 80% dry solids) and a high dextrose equivalence (typically greater than 90 D.E and most commonly 95 D.E.) can be commonly employed. Indeed, while the higher the purity of the dextrose source, the better the quality of the product (other things being equal), the catalysts of this invention allow the use of a lower purity dextrose source and yet yield a product of substantially equivalent quality as compared with prior catalysts. Because of the ready availability of glucose and its oligomers, much of the remaining description is particularly suited to the use of glucose in its various forms.

Alcohols useful in the process of this invention are hydroxyl-functional organic compounds capable of alkylating a saccharide in the "1" position. The alcohol can be naturally occurring, synthetic, or derived from natural sources and/or derivatized. Examples include monohydric alcohols (more fully discussed below) and polyhydric alcohols (e.g. ethylene glycol, propylene glycol, polyethylene glycols, polypropylene glycols, butylene glycol, glycerol, trimethylolpropane, pentaerythritol, polyester polyols, polyisocyanate polyols, and so on). Other examples include aromatic alcohols such as benzyl alcohol, phenol, substituted phenols (e.g. alkylphenols) and alkoxylates of each.

Preferred alcohols are monohydric alcohols containing from about 1 to about 30 carbon atoms. They may be primary or secondary alcohols, straight or branched chain, saturated or unsaturated (e.g. allyl alcohol, 2-ethylhexenyl alcohol and oleyl alcohol) alkyl or aralkyl alcohols, ether alcohols, cyclic alcohols, or heterocyclic alcohols. In general, these alcohols have minimal solvent power for the saccharide molecule. Examples of the monohydric alcohols which may be employed in the present invention include methyl alcohol, isopropyl alcohol, butyl alcohol, octyl alcohol, nonyl alcohol, decyl alcohol, dodecyl alcohol, tridecyl alcohol, tetradecyl alcohol, pentadecyl alcohol, hexadecyl alcohol, pentacosyl alcohol, oleyl alcohol, linoleyl alcohol, isoborneol alcohol, hydroabietyl alcohol, phenoxyethanol, phenoxypolyethoxyethanol containing five ethoxy groups, 2-methyl-7-ethyl-4-undecanol, and mixtures of one or more of the above.

A preferred group of alcohols are alkanols having the formula ROH wherein R represents an alkyl group having from 8 to 30 carbon atoms. A particularly preferred group of alcohols are those wherein R represents an alkyl radical having from 8 to 20, preferably 11 to 18, carbon atoms. The alkyls can be straight or branched chain.

The molar ratio of alcohol to monosaccharide in the reaction mixture can vary widely but is typically between about 1.5:1 to about 10:1, and preferably between about 2.0:1 to about 6.0:1. The particular molar ratio chosen depends upon the desired average degree of polymerization (DP) of the monosaccharide reacted with the alcohol. The DP represents the average number of monosaccharide derived moieties that are attached to each alkyl chain of the alkylglycosides produced. Generally, as the alcohol to monosaccharide ratio is increased, the DP decreases. Likewise, as this ratio is decreased, the DP increases. Mathematically $$DP = 1 + (f-1)/(R \times F_T),$$

where f equals 5 for glucose and is the number of hydroxyls on the saccharide ring in the cyclic acetal form, empirically R varies between about 2.0 and 3.0 for monohydric alkanols and is the glycose binding reactivity of the fatty alcohol relative to the average reactivity of available non-anomeric hydroxyl groups of the saccharide moiety and $F_T$ is the mole ratio of alcohol to available carbohydrate. Preferably, the ratio of alcohol to monosaccharide will be chosen to allow the production of an alkyl glycoside product having a DP between about 1.2 and 2.2.

With prior catalysts, low alcohol to monosaccharide ratios, i.e., ratios much less than about 1.5, were avoided for optimized reaction control. Low alcohol to monosaccharide ratios cause the occurrence of two irreversible and undesirable side reactions. For example, when glucose was used as the monosaccharide, elevated levels of glucose polymers (poly-dextrose) were often formed, especially during the latter stages of the reaction. This resulted in excessive foaming and in the loss of glucose in the reaction material, actually causing an increase in $F_T$ (the alcohol to glucose ratio) and hence a decrease in DP. The second reaction involved the dehyration of glucose into hydroxy methyl furfural (HMF) and related condensation products (e.g. polyanhydro HMF). These substances were, or lead to the formation of, color bodies which contaminated the product, preventing the further process steps from producing a substantially colorless alkylglycoside product. However, the use of a hydrophobic catalyst of this invention minimizes these reactions and, thus, much lower ratios of alcohol to monosaccharide can be employed in the present process.

With glucose as the carbohydrate, the temperature for carrying out the reaction may generally vary between about 85° C. and about 125° C., preferably between about 95° C. and about 120° C. If a temperature significantly greater than 120° C. is used, side reactions may increase faster than the primary reaction. When glucose is used, this causes a marked increase in poly-dextrose formation. The temperature generally also should not be significantly below 85° C. Such a reduced temperature causes an unacceptable reduction in reaction rate or a need for an increase in the amount of catalyst.

The reaction generally takes place in an environment which facilitates the removal of more volatile reaction by-products (e.g. water) to drive the reaction toward formation of alkyl glycosides. This environment may be conveniently maintained by reducing the equilibrium water vapor pressure under which the reacting occurs. This reduction of pressure enables more volatile reaction by-products to be evaporated from the reaction mixture. Preferably, such a reduction in pressure is achieved by applying a vacuum to the reacting system.

Preferred apparatus for applying vacuum to the reaction system includes steam jets or mechanical vacuum pumps. With higher fatty alcohols, the final vacuum preferably should be applied at a pressure between about 10 mm Hg and about 100 mm Hg. This is especially desirable when water is a reaction by-product.

If the pressure is kept significantly below 10 mm Hg, codistillation of lower alcohols may result. In addition, almost all of the water remaining in the reacting system could be evaporated. Under these circumstances, saccharide moieties, such as glucose, degrade faster, and their degradation products more rapidly form unacceptable levels of color bodies. An additional problem with vacuums below 10 mm is the inability to economically condense water vapor and the associated problems of high volumes of non-condensed vapors or contamination of vacuum pump fluids.

To neutralize the acid catalyst, an alkaline substance, preferably an alkali metal hydroxide such as sodium hydroxide, is used in an amount about equal, on a stoichiometric basis, to the amount of material needed to neutralize the catalyst. If an organic sulfonic acid catalyst is used, one mole of the alkaline substance may, for example, react with one mole of catalyst. If one mole of the alkaline substance reacts with one mole of the catalyst, e.g. when sodium hydroxide is used to neutralize the catalyst, then an amount of the sulfonate anion about equal to the amount of catalyst remains in the mixture. Such a neutralization reaction would yield one mole of neutral sodium sulfonate for each mole of catalyst and alkaline substance used.

It should be appreciated that when other acid catalysts are used—such as alkyl hydrogen sulfates—they may not be easily neutralized. The inability to determine and control neutrality with such a catalyst could cause the production of an alkyl glycoside product having an unacceptable color for household detergent uses.

For example, alkyl hydrogen sulfates (e.g. sulfuric acid mono-esters of alkanols) can undergo transesterification of the sulfate ester group with the alcohol, the alkyl glycosides and the saccharides present. These esters themselves may cause the production of color bodies. Just as important, because the amount of these esters may be variable and difficult to determine, it may be nearly impossible to calculate the amount of alkaline material needed to neutralize the sulfuric acid and its half acid esters present and to maintain neutrality during a subsequent isolation step.

If too much alkaline material is used—such as when stoichiometric amounts of a basic compound are applied to a sulfuric acid catalyzed product—then the excess alkalinity could cause monosaccharide degradation, forming base catalyzed and promoted reactions and volatile and non-volatile color bodies. Similarly, if insufficient alkaline material is added, then acid catalyzed side reactions may cause the production of color bodies during handling and/or undesired polymerization of the resulting product during isolation.

For lowest colored products, as well as for lower dialkyl ether by-products, it is desirable to maintain a certain minimum level of water in the reaction mixture at all times, but no separate aqueous phase in contact with the reaction mixture should be present. For example, when glucose monohydrate is the starting material, a small amount of water retention helps solubilize the glucose, prevents the degradation of the monosaccharide, which could otherwise accelerate, and slows down color body and ether forming condensations. In conjunction with maintaining the vacuum pressure within a specified range, it has been found that use of glucose monohydrate or glucose syrup as the monosaccharide starting material helps ensure that a preferred minimum amount of water will be present in the mixture at the time the reaction is started.

If anhydrous glucose is used instead of glucose monohydrate or glucose syrup as the monosaccharide starting material, there will be little water in the mixture before the reaction begins. After the reaction begins, water will gradually build up in the reaction mixture until the water produced becomes balanced by the water evaporated. At this time, the reaction mixture includes sufficient water, preferably about 0.1% or less based on the weight of the reaction mixture, to inhibit glucose degradation.

It should be appreciated that the actual amount of water present in the reaction mixture as the reaction takes place depends upon the pressure, type of alcohol used, the temperature applied and may also depend upon the monosaccharide starting material.

It should also be appreciated that when glucose monohydrate is used as the monosaccharide starting material, instead of anhydrous glucose, the amount of water required to prevent or minimize glucose degradation is present in the mixture prior to the beginning of the reaction; whereas when anhydrous glucose is the monosaccharide starting material, the amount of water needed to help solubilize glucose and prevent or minimize glucose degradation may not be generated until after the reaction has proceeded for a period of time.

When glucose or glucose monohydrate was used as the monosaccharide starting material with prior catalysts, it was found that an acceptable product was most often produced when the reaction was stopped before substantially all of the glucose was reacted. As an alternative to allowing the reaction to progress to completion, which for a glucose/8 to 18 carbon straight chain alcohol blend may require from about 2 to about 10 hours, one often chose, with prior catalysts, to allow the reaction to proceed until, for example, about 0.1% to about 3% of the glucose starting material remained. The time needed to achieve this extent of reaction was from about 1.5 to about 6 hours when an 8 to 18 carbon straight chain alcohol was reacted with the glucose. The advantage from shortening the reaction time was that the less time the reaction proceeds, the more kinetically controlled the process and the lesser the amount of undesirable by-products produced. However, the use of a hydrophobic catalyst of this invention allows one to allow the reaction to proceed to substantial completion with precise control of the reaction and minimization of undesirable by-products.

If it is desirable to stop the reaction prior to substantial completion, an amount of a reducing agent such as $NaBH_4$ (sodium borohydride) may be added to ensure that the remaining glucose will not react to produce unwanted by-products. Functionally, the $NaBH_4$ reduces the excess glucose to sorbitol, and other reducing sugars to their corresponding alditols. Preferably at least about 1 gram of $NaBH_4$ is added for every 10 to 20 grams of excess glucose. Using $NaBH_4$ to hydrogenate the excess glucose has been found in some cases to be more efficient than to bleach the product that would hydrogenate the excess glucose has been found in some cases to be more efficient than to bleach the product that would otherwise result if the glucose had not been converted to sorbitol.

After neutralization of the acid catalyst, and optional reduction of excess saccharide, it is generally desirable to remove the excess unreacted alcohol. Alcohol removal is generally accomplished by evaporation, e.g. distillation, of the alcohol. The use of a wiped film evaporator is particularly convenient for this purpose, e.g. operated at about 160°–170° C. and about 96.7 Pa (0.5 mm Hg) pressure.

In ascertaining and/or quantifying the color (i.e., the relative darkness or lightness) characteristics of aqueous glycoside solutions produced in the process of the present invention, it is convenient to utilize the extinction coefficient of the glycoside material of interest using a suitable spectrophotometer (e.g. a Spectronic 20) over a path length of 1 cm and using 470 nm wavelength light. Since the extinction coefficient is essentially a measure of the ability of the glycoside solution of concern to absorb light as opposed to transmitting same, small extinction coefficients correspond to substantially colorless glycoside solutions. Accordingly, the process of the present invention has the effect of producing an alkyl glycoside product having a reduced extinction coefficient.

The term "extinction coefficient" as used herein refers to the calculated absorbance of a theoretical solution containing one gram of solid material per $cm^3$ of solution measured as described above and calculated according to the following formula:

$$E_{470} = A/(c \times 1)$$

wherein: A = measured absorbence @470 nm c = concentration in grams per $cm^3$ l = path length in centimeters.

While not being a required or overriding feature or parameter of the present invention, it can be stated as a general point of reference that dark colored glycoside solutions, such as are produced in other processes for making an alkyl glycoside product, can have extinction coefficients of over 20, whereas the extinction coefficient of the alkyl glycoside product made in the present invention is generally less than 2.5, and more typically less than 1.0.

The following examples will serve to illustrate various aspects of the invention and should not be construed as limiting the invention. All parts, ratios and percentages set forth above or below are by weight unless otherwise indicated in context.

The process of the invention produces an alkyl glycoside material with a monomodal distribution of polymeric alkyl glycosides not obtainable by other processes. The product of the invention is novel.

EXAMPLES

Example 1

A one-liter, four-necked, round-bottomed flask was equipped through its center neck with an overhead mechanical stirrer, through a second neck with a distillation head fitted with an addition funnel and a condenser/receiver/vacuum take-off assembly, through a third neck fitted with a three hole rubber stopper with a capillary nitrogen bleed, a calibrated mercury thermometer and a vacuum tight temperature controller probe, and on the fourth neck with a septum for sampling.

The flask was charged with 602.4 g (3.105 moles) of a commercial mixture of $C_{11}$ to $C_{15}$ (98% $C_{12}$ and $C_{13}$) straight and branched alkanols (Neodol TM 23 available form Shell Chemical Co.) and 136.6 g (0.69 moles) of a commercially available dextrose monohydrate (Staleydex 333, available from A. E. Staley Mfg. Co. at 9.0% moisture). The slurry was heated at a vacuum of 30 mm Hg (absolute). Water was released starting at about 57° C. and heating was continued until the slurry had reached 110° C. At this time 3.2 g (0.00345 mole of a commercially available mixture of 50% dinonylnaphthalenesulfonic acid in heptane (available from King Industries) was added as a catalyst and the theoretical volume of water distilled at about a linear rate over 8 hours. After stirring an additional hour, a stoichiometric amount of aqueous NaOH (33% in $H_2O$) was added. An aliquot of the neutralized reaction mixture (3.39 g, 1 g dissolved substance) was dissolved in a total volume of 10 ml with 1:1 isopropanol:water. The pH of this solution was 7.8 and the absorbance at 470 nm was 0.05 ($E_{470}=0.50$).

The remainder of the reaction mixture was evaporated to a clear melt @ 200° C. and 1 mm pressure using a Leybold-Heraeus Distact TM wiped film evaporator operating at a feed rate of 700 ml/hr.

The residue was analyzed using a combination of gas and liquid chromatographic techniques as well as NMR spectroscopy and was shown to contain less than 0.2% free alcohol and less than 2% polar species (HPLC) and an NMR mole ratio of glucose rings to fatty chains of about 1.4.

Examples 2 and 3 and Comparative Examples A-D

Examples 2 and 3 and Comparative Examples A-D were run in an identical manner and substantially as described in Example 1 with the exceptions noted in Table 1, below. The comparative catalysts were paratoluenesulfonic acid (PTSA) available from Eastman Kodak Company as the monohydrate and dodecylbenzenesulfonic acid (HLAS) available from Pilot Chemical Company as 97-99% active. The results are also shown in Table 1.

The decrease in total polar species (i.e. polydextrose and high oligomers of alkyl glycosides) for DNNSA as compared with both pTSA and HLAS is a definite process advantage, particularly with respect to further processing such as distillation of the fatty alcohol where polar species are susceptible to decomposition. Because each reaction was run to the same endpoint with respect to residual dextrose (i.e.less than 1% of original) and because the runs which employed DNNSA and pTSA reached the endpoint after the runs which employed HLAS, the runs with DNNSA and pTSA were slower with respect to consumption of dextrose than the runs with HLAS.

We claim:

1. A process of preparing glycosides comprising reacting in the presence of an acid catalyst, an alcohol with a source of saccharide moiety, wherein the acid catalyst comprises a strong hydrophobic organic acid having an HLB of less than the HLB of alkylbenzenesulfonic acids having 15 aliphatic carbon atoms, alkylsulfonic acids having 22 aliphatic carbon atoms and alkylnaphthalenesulfonic acids having 8 aliphatic carbon atoms.

2. A process of claim 1 wherein the acid catalyst is an acid composition wherein essentially all strong acids have an HLB of less than the HLB of alkylbenzenesulfonic acids having 15 aliphatic carbon atoms, an alkylsulfonic acid having 22 aliphatic carbon atoms, and alkylnaphthalenesulfonic acids having 8 aliphatic carbon atoms.

3. A process of claim 1 wherein the acid catalyst is comprised of at least one member selected from the group consisting of:
   (a) Alkyl hydrogen sulfates having at least 23 aliphatic carbon atoms;
   (b) alkylbenzenesulfonic acids having at least 16 aliphatic carbon atoms,
   (c) alkylnaphthalenesulfonic acids having at least 9 aliphatic carbon atoms;
   (d) alkylsulfonic acids having at least 23 aliphatic carbon atoms,
   (e) alkylarols having sufficient electron withdrawing substituents to render said alkylarol a strong acid;
   (f) copolymers of styrenesulfonic acid and a hydrophobic, mono-olefinic comonomer; and
   (g) di alkyl esters of sulfo succinic acids having at least a total of 10 carbon atoms in the alkyl groups.

4. A process of claim 3 wherein the acid catalyst is comprised of a member selected from the group consisting of: (a) an alkylnaphthalenemonosulfonic acid having at least one alkyl group containing a total of at least 9 carbon atoms, and (b) a copolymer comprised of styrene sulfonic acid and a hydrophobic, mono-olefinic comonomer.

5. A composition of matter comprising a mixture of glycosides produced by the process of claim 1.

TABLE 1

| | Run Molar Ratios: Carbohydrate | | | Temp. °C. | Pressure Total mm Mercury | Polars % D.S. | Time Hours |
|---|---|---|---|---|---|---|---|
| | Neodol 23/Carbohydrate/Catalyst | Source | Catalyst | | | | |
| 1 | 5.3/1.0/0.010 | STA 333 | pTSA | 105 | 30 | 4.8 | 9.0 |
| 2 | 5.0/1.0/0.010 | STA 333 | HLAS | 105 | 30 | 3.2 | 8.0 |
| 3 | 5.0/1.0/0.10 | STA 333 | DNNSA | 105 | 30 | 2.2 | 9.0 |
| 4 | 5.0/1.0/0.010 | * | pTSA | 105 | 30 | 8.0 | 8.0 |
| 5 | 5.0/1.0/0.011 | * | HLAS | 105 | 30 | 5.9 | 6.5 |
| 6 | 5.0/1.0/0.10 | * | DNNSA | 105 | 30 | 3.4 | 8.0 |

*95 dextrose equivalent corn syrup solids

6. A process of claim 1 wherein the acid catalyst has less than 2% of a source of sulfuric acid, said 2% being on the basis of weight as sulfuric acid by weight of said acid catalyst.

7. A process of claim 1 wherein the acid catalyst is essentially free of a source of sulfuric acid.

8. A process for preparing glycosides comprising:
(a) reacting, to form an acid catalyst, a composition comprised of an organic-sulfonic acid and a source of sulfuric acid, with a material reactive with the source, the amount of the reactive material being (i) sufficient to convert at least a portion of the source of sulfuric acid to a member selected from the group consisting of hydrophobic acids, non-acidic salts, and mixtures thereof, and (ii) insufficient to convert the majority of the organic-sulfonic acid in the composition to an organic-sulfonate, and
(b) reacting, in the presence of the acid catalyst, an alcohol having more than four carbon atoms with a source of saccharide moiety.

* * * * *